United States Patent
Azuma et al.

(10) Patent No.: US 8,353,836 B2
(45) Date of Patent: Jan. 15, 2013

(54) ULTRASONOGRAPHIC DEVICE FOR PERFORMING LUMINANCE CORRECTION

(75) Inventors: Takashi Azuma, Kawasaki (JP); Shin-ichiro Umemura, Muko (JP); Hideyo Kamada, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 1046 days.

(21) Appl. No.: 11/597,325

(22) PCT Filed: Nov. 10, 2004

(86) PCT No.: PCT/JP2004/016631
§ 371 (c)(1), (2), (4) Date: Sep. 17, 2008

(87) PCT Pub. No.: WO2005/115248
PCT Pub. Date: Dec. 8, 2005

(65) Prior Publication Data
US 2009/0163816 A1    Jun. 25, 2009

(30) Foreign Application Priority Data
May 26, 2004    (JP) .................................. 2004-155662

(51) Int. Cl.
*A61B 8/00* (2006.01)
*G06K 9/00* (2006.01)
(52) U.S. Cl. ......... 600/443; 382/128; 382/133; 600/437
(58) Field of Classification Search .................. 600/449, 600/454, 455, 441, 442, 443; 128/916; 382/128, 382/130, 133, 134
See application file for complete search history.

(56) References Cited

U.S. PATENT DOCUMENTS

| 4,787,395 | A |   | 11/1988 | Yanashima et al. |
|---|---|---|---|---|
| 4,967,753 | A | * | 11/1990 | Haase et al. ................... 600/468 |
| 5,271,404 | A | * | 12/1993 | Corl et al. ..................... 600/454 |
| 6,142,943 | A |   | 11/2000 | Mo et al. |

(Continued)

FOREIGN PATENT DOCUMENTS

JP    04-051941    2/1992

(Continued)

*Primary Examiner* — Long V. Le
*Assistant Examiner* — Helene Bor
(74) *Attorney, Agent, or Firm* — Antonelli, Terry, Stout & Kraus, LLP.

(57) ABSTRACT

The present invention provides an ultrasonic diagnostic apparatus realizing improved visibility of a contour shape of signal components in an ultrasonic blood flow spectrum display image. The apparatus includes a gray-level correction unit for correcting intensity of an output result of a Doppler processing unit. The Doppler processing unit calculates a Doppler frequency shift in a reception signal output from a receiver and calculates blood flow velocity of a subject on the basis of the Doppler frequency shift. The gray-level correction unit has: a filtering unit for separating a signal and a noise from each other, which are included in a time-varying waveform of the blood flow velocity of the subject obtained by the Doppler processing unit on the basis of continuity on a space defined by the blood flow velocity and time; and a gray-level corrector for performing a gray level correction using, as a parameter, a boundary value between signal intensity and noise intensity obtained by the filtering unit.

6 Claims, 10 Drawing Sheets

U.S. PATENT DOCUMENTS

| | | | |
|---|---|---|---|
| 6,447,455 B2 * | 9/2002 | Bang et al. | 600/454 |
| 6,500,125 B1 * | 12/2002 | Muzilla et al. | 600/454 |
| 2004/0073112 A1 | 4/2004 | Azuma et al. | |
| 2006/0052698 A1 * | 3/2006 | Loupas | 600/437 |

FOREIGN PATENT DOCUMENTS

| | | |
|---|---|---|
| JP | 11-033024 | 2/1999 |
| JP | 2000-262520 | 9/2000 |
| JP | 2000-262820 | 9/2000 |
| JP | 2000-300561 | 10/2000 |
| JP | 2002-534185 | 10/2002 |
| JP | 2004-129773 | 4/2004 |
| WO | WO 00/40998 | 7/2000 |

* cited by examiner

HISTOGRAM OF INTENSITY
DIFFERENCE OF ADJACENT PIXELS

FIG.4B

WEIGHTING FUNCTION 1

ORIGINAL IMAGE

FIG.7B

THE PRESENT INVENTION

FIG.7C

CONVENTIONAL METHOD

PRIOR ART

PRIOR ART

ULTRASONOGRAPHIC DEVICE FOR PERFORMING LUMINANCE CORRECTION

TECHNICAL FIELD

The present invention relates to an ultrasonographic technique and, more particularly, to an ultrasonographic device having the function of detecting blood flow velocity in a living body on the basis of Doppler frequency shift in a reception signal from a subject.

BACKGROUND ART

An ultrasonic diagnostic apparatus transmits an ultrasonic beam from a ultrasonic probe to a subject, and obtains information necessary for diagnosis on the basis of a reception signal from the subject. For example, a Doppler frequency shift in a reception signal is detected and, on the basis of the Doppler frequency shift, the velocity of blood flow can be obtained.

Figure 9:
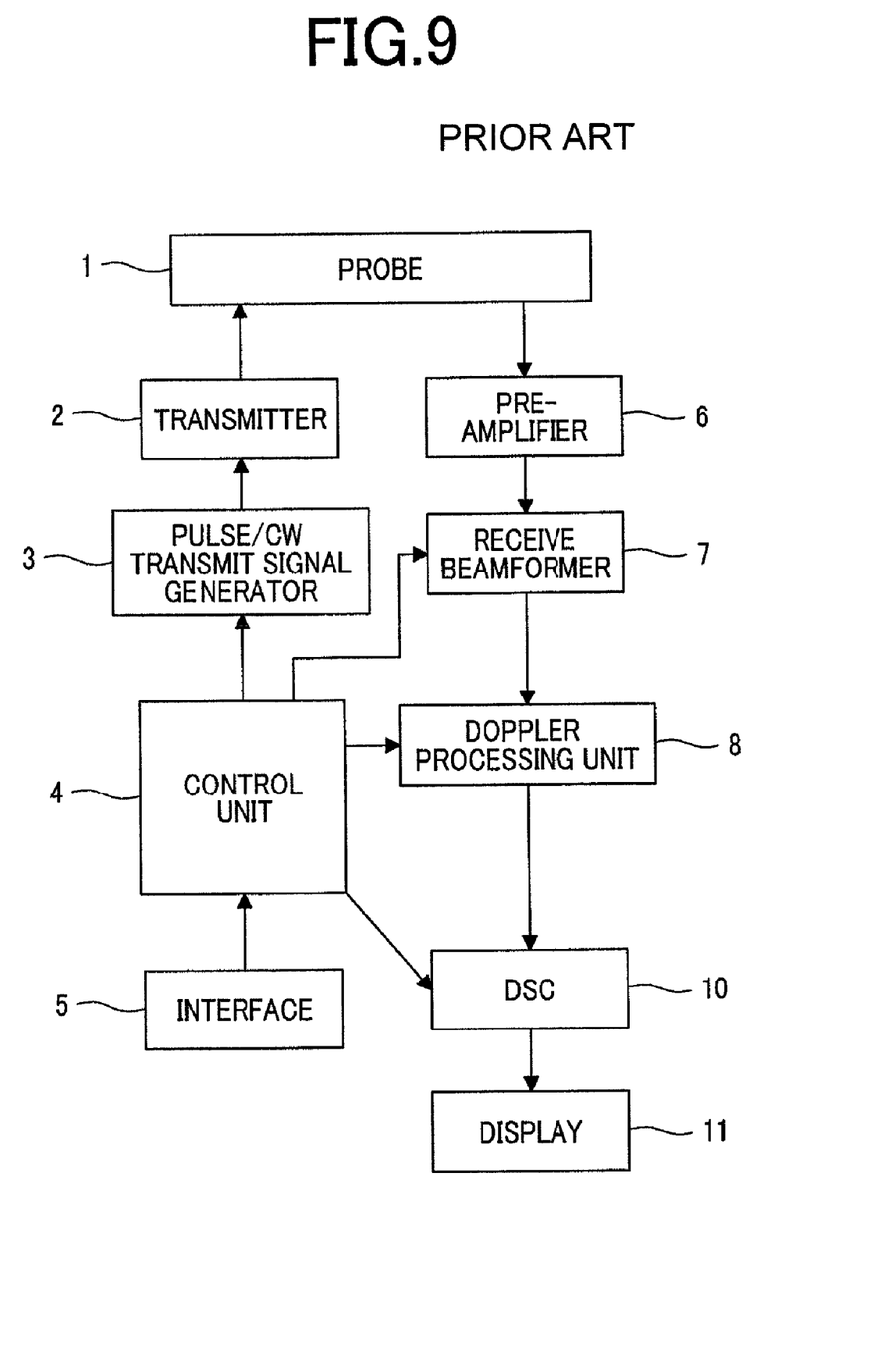
FIG. 9 is a diagram illustrating the configuration of a conventional ultrasonic diagnostic apparatus.

Such an ultrasonic Doppler apparatus has, as shown in FIG. 9, a probe 1 for transmitting/receiving ultrasonic wave, an interface 5 for operating an ultrasonic diagnostic apparatus, a control unit 4 for controlling the whole system, a pulse/CW transmit signal generator 3 for generating a transmission waveform on the basis of the control unit 4, a transmitter 2 for amplifying a signal generated by the pulse/CW transmit signal generator 3, a pre-amplifier 6 for amplifying a reception signal from the probe 1, a receive beamformer 7 for selectively emphasizing a signal from a desired location, a Doppler processing unit 8 for detecting a Doppler shift component from the blood flow from a phase output, a digital scan converter (DSC) 10 for displaying an instantaneous frequency component calculated by the processing unit as blood flow waveform data, and a display 11 for displaying an output of the scan converter.

In such an ultrasonic Doppler apparatus, when ultrasonic wave having a frequency $f_0$ is output from the probe 1, since blood of the subject flows at predetermined speed, an echo signal obtained by the ultrasonic wave from the probe 1 reflected by blood cells has been subjected to a frequency shift by the Doppler effect. The Doppler processing unit 8 detects the Doppler shift component (Doppler signal). Since the blood flow velocity varies, a Doppler signal obtained includes different frequency components. The Doppler processing unit 8 obtains a frequency distribution, that is, blood flow distribution by performing a method such as fast Fourier transform on the Doppler shift component. By sequentially performing the computation, a change with time in the blood flow distribution is displayed. The method provides significant data also from the clinical viewpoint and is widely used. In particular, the data can be used not only as quantitative data of the maximum blood flow velocity in a predetermined position in a subject but also as data in the case of diagnosing a valvular disease of the heart or the like. By displaying a time-varying waveform of a velocity distribution of the blood flow from the portion of the valve of the heat, backflow at the valve can be determined. The shape itself of the time-varying waveform of the blood flow velocity distribution is widely known as data useful for diagnosis.

Since a Doppler signal is based on a reflection signal from a blood cell having low ultrasonic scattering power, there has been the task of improving a signal-to-noise ratio. Noise exists also in a velocity range in which signals do not inherently exit in the time-varying waveform of the blood flow velocity distribution, and it largely deteriorates visibility of the time-varying waveform of the blood flow velocity distribution. As a method of solving the problem, for example, a method of setting a threshold between an area including many noise components and an area including many signal components at the time of performing gray scale mapping has been proposed (refer to, for example, Published Japanese Translation of PCT International Publication for Patent Application No. 2002-534185). The gray scale mapping is a method of displaying a change with time of a blood flow velocity distribution by setting time on the axis of abscissa, velocity on the axis of ordinate, and intensity of a signal as brightness.

DISCLOSURE OF INVENTION

Problem to be Solved by the Invention

The gray scale mapping is performed on assumption that two peaks basically appear in the intensity of the signal component showing blood flow velocity and the intensity of the noise component. In reality, however, signals of low intensity are also included in the signal components, so that the components cannot be separated to the signal component and the noise component on the basis of the intensity. Consequently, when an output of a low-intensity signal is suppressed, the intensity of the signal components becomes partially low, the contour shape of a spectrum waveform is deformed, and a so-called black spot in which a signal drops occurs.

Therefore, an object of the present invention is to provide an ultrasonic diagnosis apparatus realizing improved visibility of a contour shape of signal components in an ultrasonic blood flow spectrum display image.

Means for Solving the Problem

To achieve the object, an ultrasonic diagnostic apparatus of the present invention has the following characteristics.

(1) An ultrasonic diagnostic apparatus of the present invention has: an ultrasonic probe; a transmitter having a transmission signal generating circuit for generating a ultrasonic wave made by continuous wave or pulse wave and selectively transmitting the ultrasonic wave to a subject via the ultrasonic probe; a receiver for phasing a reception signal received from the subject by the ultrasonic probe; a Doppler processing unit for calculating Doppler frequency shift in the reception signal output from the receiver and calculating blood flow velocity of the subject on the basis of the Doppler frequency shift; a display for displaying a waveform of the blood flow velocity; a controller for controlling the transmitter, the receiver, the Doppler processing unit, and the display; and a gray-level correcting unit for correcting gray level of an output result of the Doppler processing unit, wherein the gray-level correcting unit includes: a filtering unit for separating a signal and a noise from each other, which are included in a time-varying waveform of the blood flow velocity of the subject obtained by the Doppler processing unit on the basis of continuity on a space defined by the blood flow velocity and time; and a gray-level corrector for performing a gray level correction using, as a parameter, a boundary value between signal intensity and noise intensity obtained by the filtering unit.

(2) In the ultrasonic diagnostic apparatus of (1), the gray-level correction unit is constructed so as to suppress an intensity signal lower than the boundary value in intensity distribution of the signal and the noise.

(3) In the ultrasonic diagnostic apparatus of (1), the filtering unit has: means for defining a peripheral pixel range of a pixel in image data on the blood flow velocity; and means for determining a weighting function from the difference between the intensity of each of the pixels and the intensity of each of the peripheral pixels, the weighting function has a maximum point at zero, an integral value of an absolute value of the function in the range from negative infinity to positive infinity is finite, and a value obtained by using sum of product of the weighting function and the intensity of each of the peripheral pixels as intensity of a pixel in image data on the blood flow velocity is used as signal intensity of a result of the filtering process.

(4) An ultrasonic diagnostic apparatus of the present invention includes: an ultrasonic probe; a transmitter having a transmission signal generating circuit for generating a ultrasonic wave made by continuous wave or pulse wave and selectively transmitting the ultrasonic wave to a subject via the ultrasonic probe; a receiver for phasing a reception signal received from the subject by the ultrasonic probe; a Doppler processing unit for calculating Doppler frequency shift in the reception signal output from the receiver and calculating blood flow velocity of the subject on the basis of the Doppler frequency shift; a display for displaying a waveform of the blood flow velocity; a controller for controlling the transmitter, the receiver, the Doppler processing unit, and the display; and a gray-level correcting unit for correcting gray level of an output result of the Doppler processing unit, wherein the gray-level correcting unit separates a signal and a noise from each other which are included in a time-varying waveform of the blood flow velocity of the subject obtained by the Doppler processing unit on the basis of a statistical property, and performs an intensity correction by suppressing output intensity equal to or lower than a boundary point between signal intensity and noise intensity obtained as a result of the filtering process.

(5) In the ultrasonic diagnostic apparatus in any of (1) to (4), the separating process includes a process for separating the signal and the noise as peaks on a histogram from each other.

Effects of the Invention

According to the present invention, in an ultrasonic blood flow spectrum display image, by suppressing intensity of noise components while minimizing the influence on display of signal components, visibility of the contour shape of the signal components is improved.

BEST MODE FOR CARRYING OUT THE INVENTION

An embodiment of the present invention will be described in detail hereinbelow with reference to the drawings.

Figure 1:
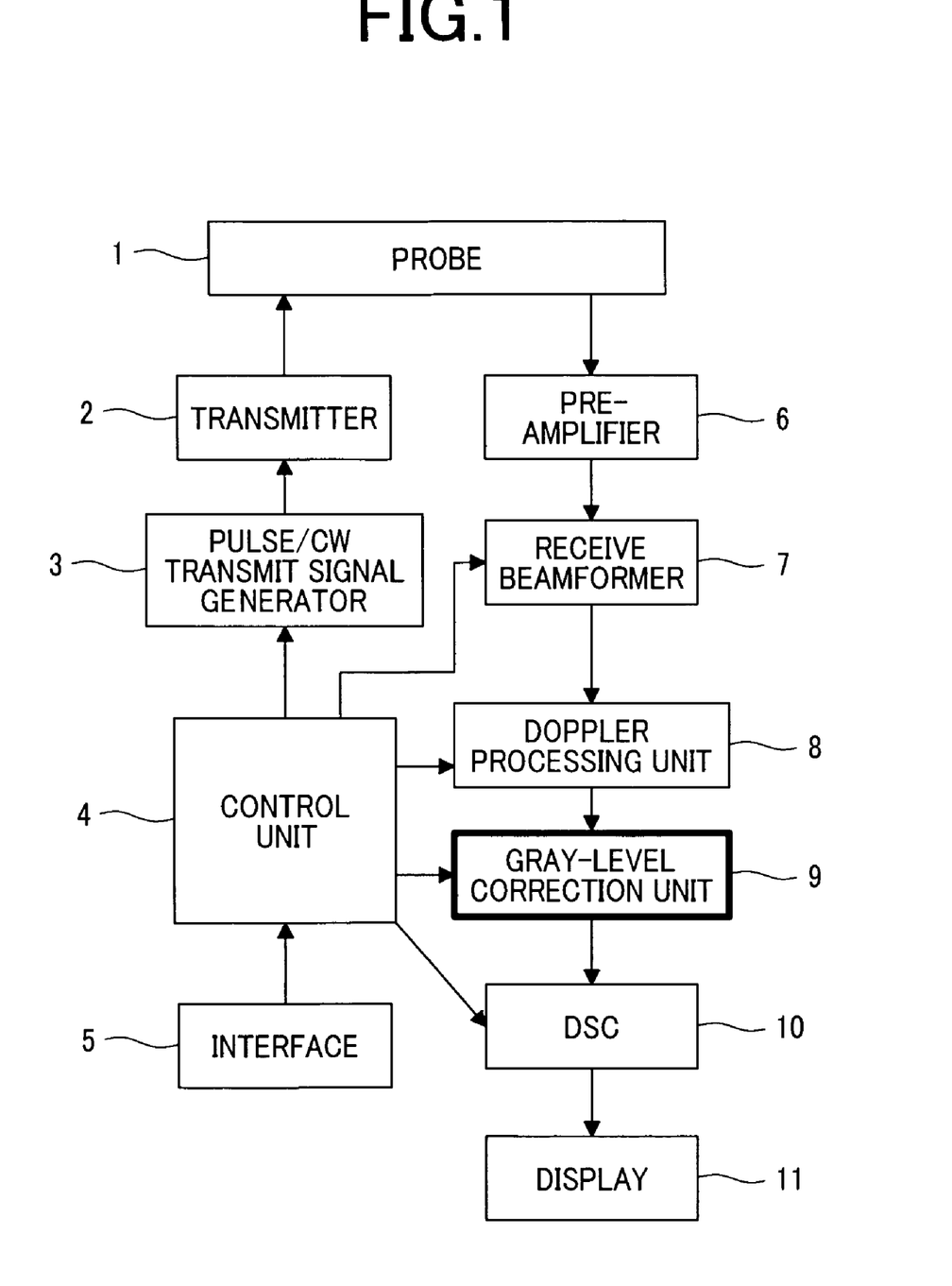
FIG. 1 is a diagram illustrating a configuration example of an ultrasonic diagnostic apparatus according to an embodiment of the present invention.

FIG. 1 shows a configuration example of an ultrasonic diagnostic apparatus as an embodiment of the invention. The apparatus has a probe 1 for transmitting/receiving ultrasonic wave to/from a subject (not shown), a control unit 4 for controlling the whole system, a pulse/CW transmit signal generator 3 for generating a transmission waveform on the basis of the control unit 4, a transmitter 2 for amplifying a signal generated by the pulse/CW transmit signal generator 3, a pre-amplifier 6 for amplifying a reception signal from the probe, a receive beamformer 7 for selectively emphasizing a signal from a desired position, a Doppler processing unit 8 for detecting a Doppler shift component from the blood flow from a phase output, a digital scan converter (DSC) 10 for displaying an instantaneous frequency component calculated by the processing unit as blood flow waveform data, and a display 11 for displaying an output of the scan converter. Particularly, in the present invention, a gray-level correction unit 9 is provided to improve visibility of a blood flow spectrum image which is output to the display 11.

Figure 2:
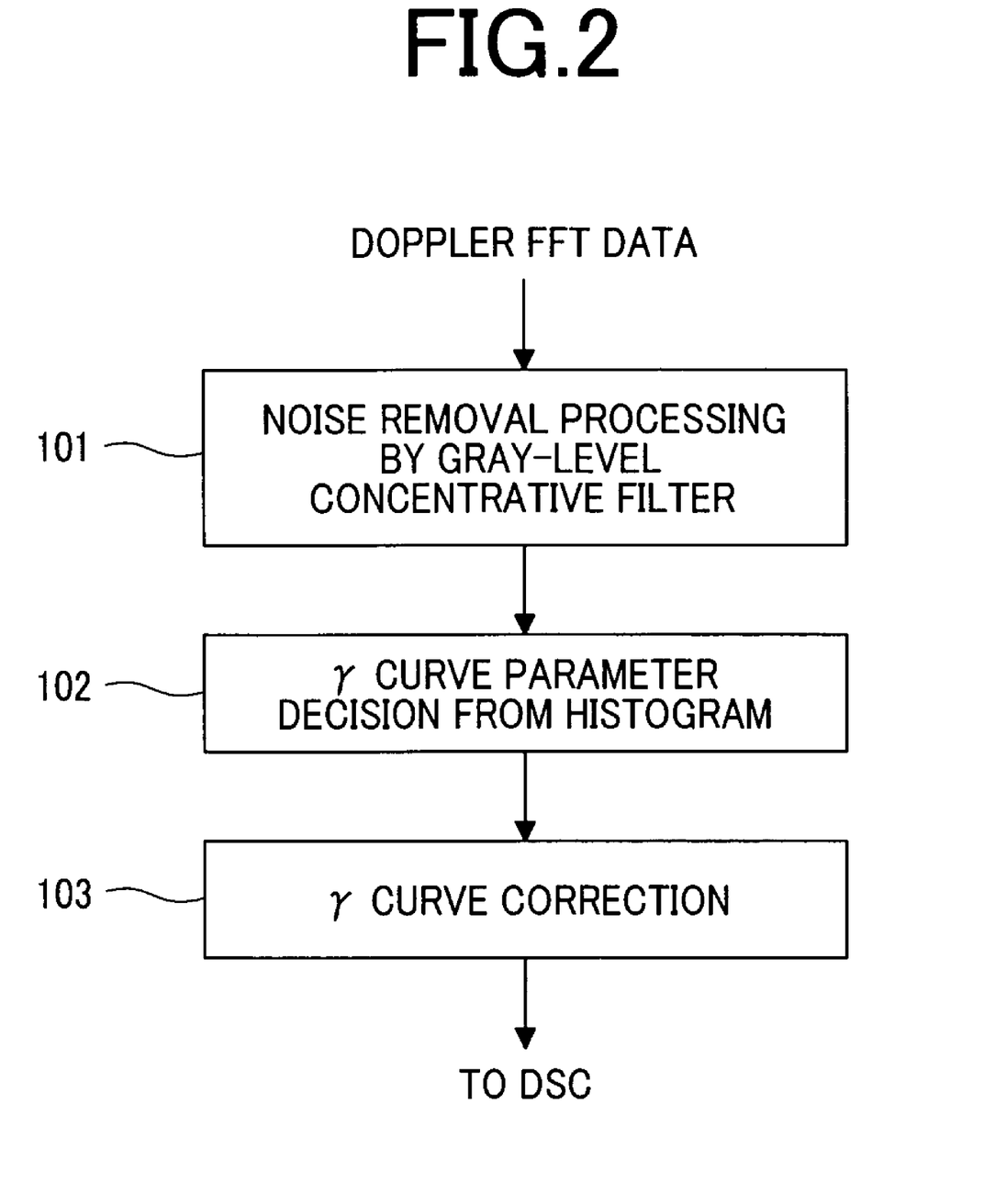
FIG. 2 is a diagram showing an intensity correcting computing process flow according to the invention.

FIG. 2 is a diagram showing a calculation processing flow executed by the gray-level correction unit 9. The intensity correction computing process is constructed by two processes; a process for separating a noise and a signal, and an intensity correcting process for suppressing output intensity equal to or less than a boundary point between the noise and the signal intensity obtained as a result of the separating process. The above-described conventional technique (Patent Document 1) employs only the intensity correcting process. In the present invention, as a pre-process of the intensity correcting process, a process for separating noise and signal from each other is also employed.

The two process flows are performed, in a concrete example, by a noise eliminating process 101 using a gray-level concentrative filter, a parameter determining process 102 of a γ curve (intensity correction curve) from a histogram from which noise has been eliminated, and a γ curve correcting process 103, thereby completing the intensity correction computing process.

Figure 3:
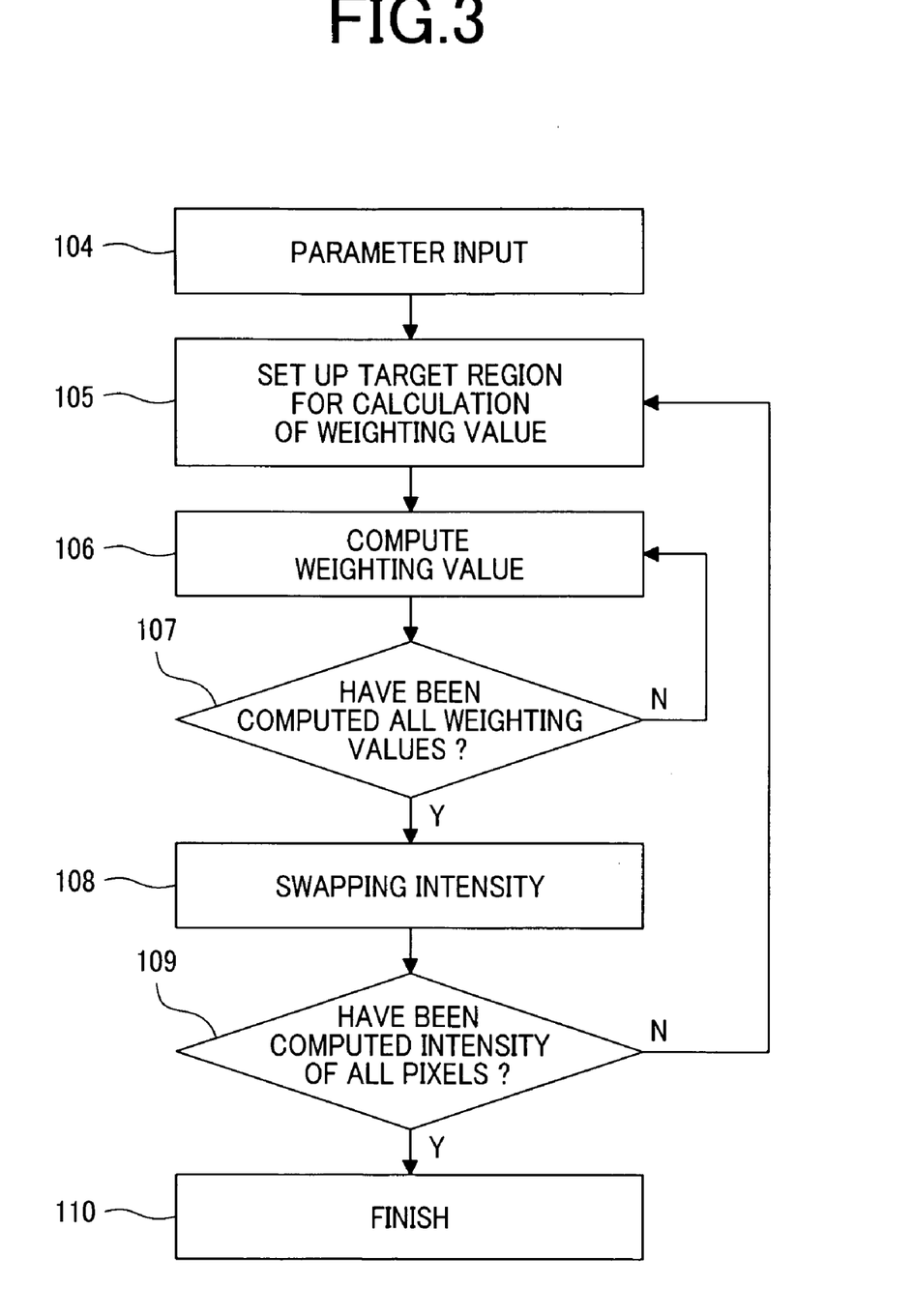
FIG. 3 is a diagram showing a process flow of a gray-level concentrative filter in FIG. 2.
Figure 10A:
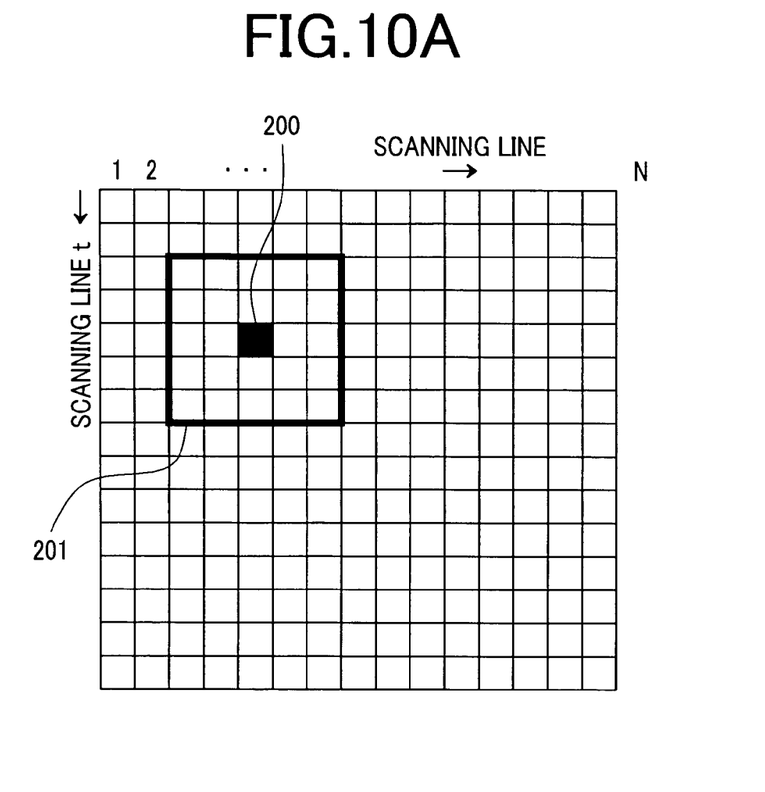
FIGS. 10A and 10B are diagrams showing image data which is input to the gray-level concentrative filter.
Figure 10B:
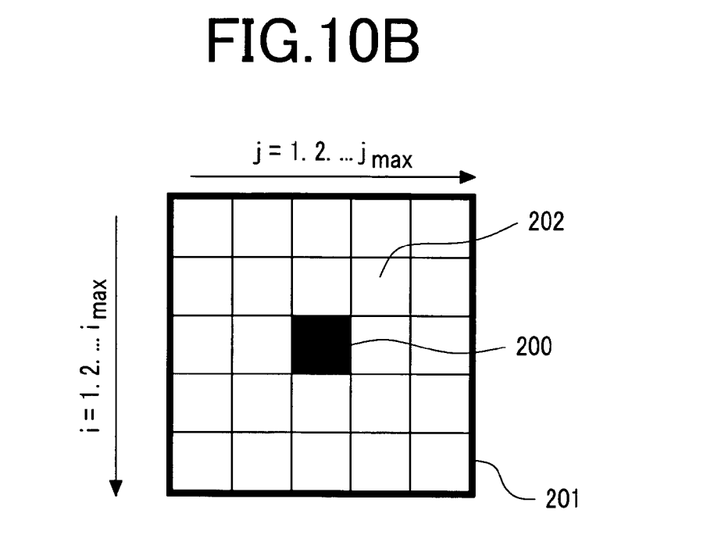

FIG. 3 shows concrete calculation process of the noise eliminating process 101 performed by the gray-level concentrative filter. FIGS. 10A and 10B show image data which is input to the gray-level concentrative filter.

In FIGS. 10A and 10B, intensity of a point (focused pixel) 200 at which intensity is calculated in image data is expressed as $I_0$, and the size of a focused area 201 (area in which a weighting value is calculated) for calculating an output of the intensity is expressed as i×j. The larger the size is, the more the gray-level concentrative filter is effective, however, the computation speed decreases only by the amount. 202 denotes peripheral pixels of the focus pixel 200 in the area 201 in which a weighting value is calculated. In place of enlargement of the size i×j of the focused area 201, it is also effective to increase efficiency of computation by performing a process of reducing the number of sampling points by decimation prior to the process of the gray-level concentration filter and increasing the number of sampling points to the original number by interpolation after the process. The number of re-sampling points of the decimation, "i" and "j", and the shape of a weighting function are determined in a parameter setting step 104 in FIG. 3. The position of a pixel of calculation and the pixels in the range determined by "i" and "j" are set in step 105, and a weighting value is calculated in step 105 on the basis of the weighting function which will be described later. By performing the weighting value calculation on all of the points (step 107), an intensity value is obtained (step 108). After $I_0$ is shifted in the image and the calculation is executed on all of the points in the image, the gray-level concentrative filter process is finished in step 109.

Figure 4A:
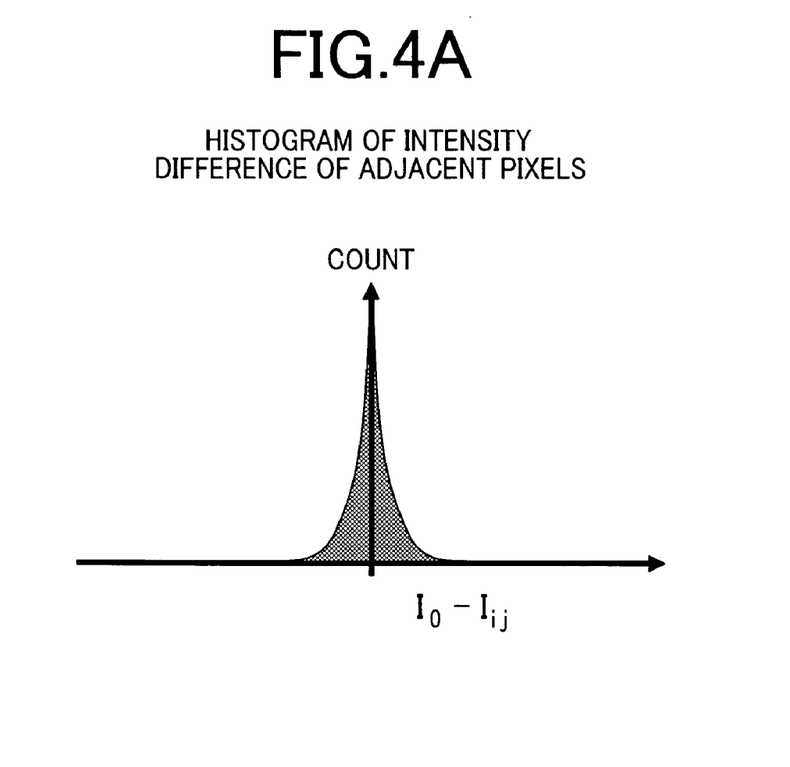
FIGS. 4A and 4B are diagrams illustrating the shapes of the frequency distribution of intensity difference and the weighting function.
Figure 4B:
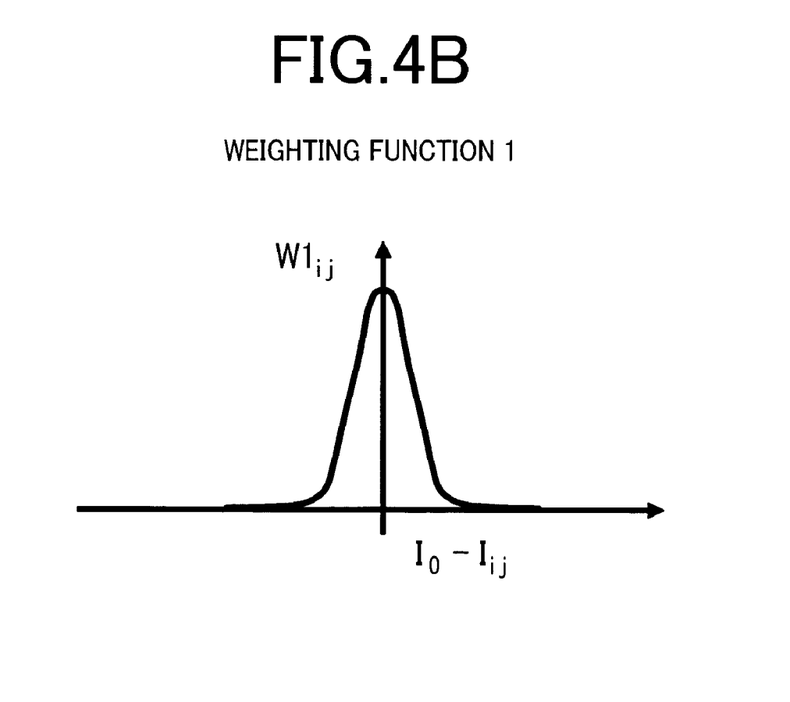

The weighting function will be described with reference to FIGS. 4A and 4B. FIG. 4A shows the frequency distribution of the intensity difference between pixels in a typical ultrasonic image. In contrast, as a function in which the weighting value monotonously decreases as the difference between $I_0$ and $I_{ij}$ increases, as shown in FIG. 4B, a Gaussian function (Equation 1) or a polynomial of even-number order can be used.

$$w_{ij} = \exp\left(-1 \times \left(\frac{I_{ij} - I_0}{\alpha}\right)^2\right) \quad \text{Equation 1}$$

In Equation 1, $\alpha$ denotes half width of a Gaussian value. When the half width, that is, $\alpha$ is increased, a change in the weighting value decreases relative to a change in intensity. As a result, sensitivity to a change in intensity decreases.

An intensity computing process shown by Equation 2 using the weighting function $W_{ij}$ is performed. In the intensity computing process, all of values obtained by multiplying the pixels in the area of calculation with the weighting function are added, and normalization is performed with the total value. As a result, new image intensity ($I'_0$) in which noise components are suppressed without blurring an image is obtained. The application of the weighting function according to the intensity difference is equivalent to two-dimensional filter process of low pass type performed along the edge of a contour shape in an image.

The gray-level concentrative filter is also called a self-centered filter by the inventors of the present invention by paying attention to the characteristic of the filter. Specifically, a large weight is given to a pixel whose property is close to a focused target pixel, so that feedback is obtained only from pixels close to the target pixel and it is similar to a behavior with self-centered will.

$$I_0 = \frac{\sum I_{ij} w_{ij}}{\sum w_{ij}} \quad \text{Equation 2}$$

Figure 5A:
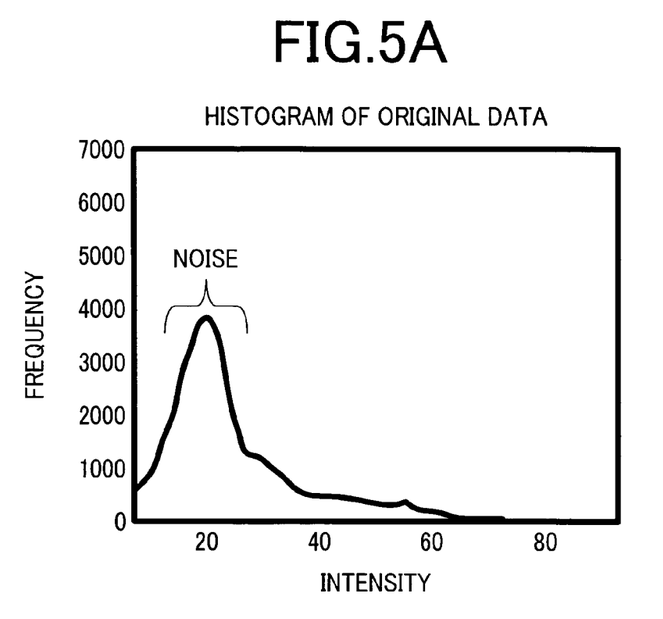
FIGS. 5A and 5B are diagrams illustrating histograms before and after a gray-level concentrative filter process in the invention.
Figure 5B:
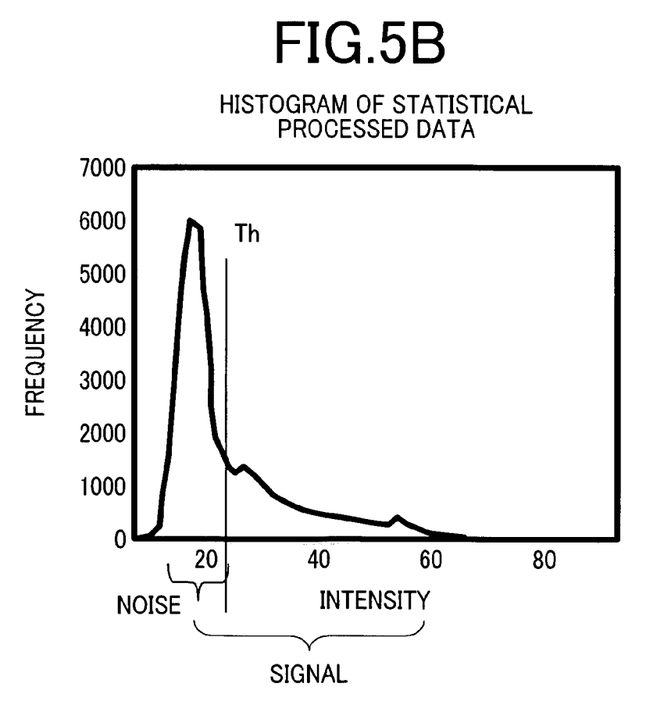

The histograms of a signal before and after the filtering process with the gray-level concentrative filter will be compared with each other by using FIGS. 5A and 5B. FIG. 5A shows the histogram of original data. A distribution of a noise signal having a peak at around 20 in intensity is the largest. There is a signal distribution on the higher intensity side. However, the peak is hidden in the noise signal distribution, and it is difficult to determine the distribution shape. On the other hand, FIG. 5B shows the histogram after the filtering process using the gray-level concentrative filter. The distribution of signal components having the peak at around intensity 25 can be clearly distinguished from the distribution of noise components. It shows that the filtering process using the gray-level concentrative filter of the present invention is different from the process of simply suppressing a low-intensity component as described in the conventional technique (Patent Document 1). In the case of giving a unique intensity output to an intensity input, signals are not separated while forming peaks. The value at which the signal distribution and the noise distribution are separated from each other in FIG. 5B is set as Th. For example, the value can be determined as Th=(M1+M2)/2 where M1 denotes the maximum value of the signal distribution and M2 denotes the maximum value of the noise distribution.

Figure 6:
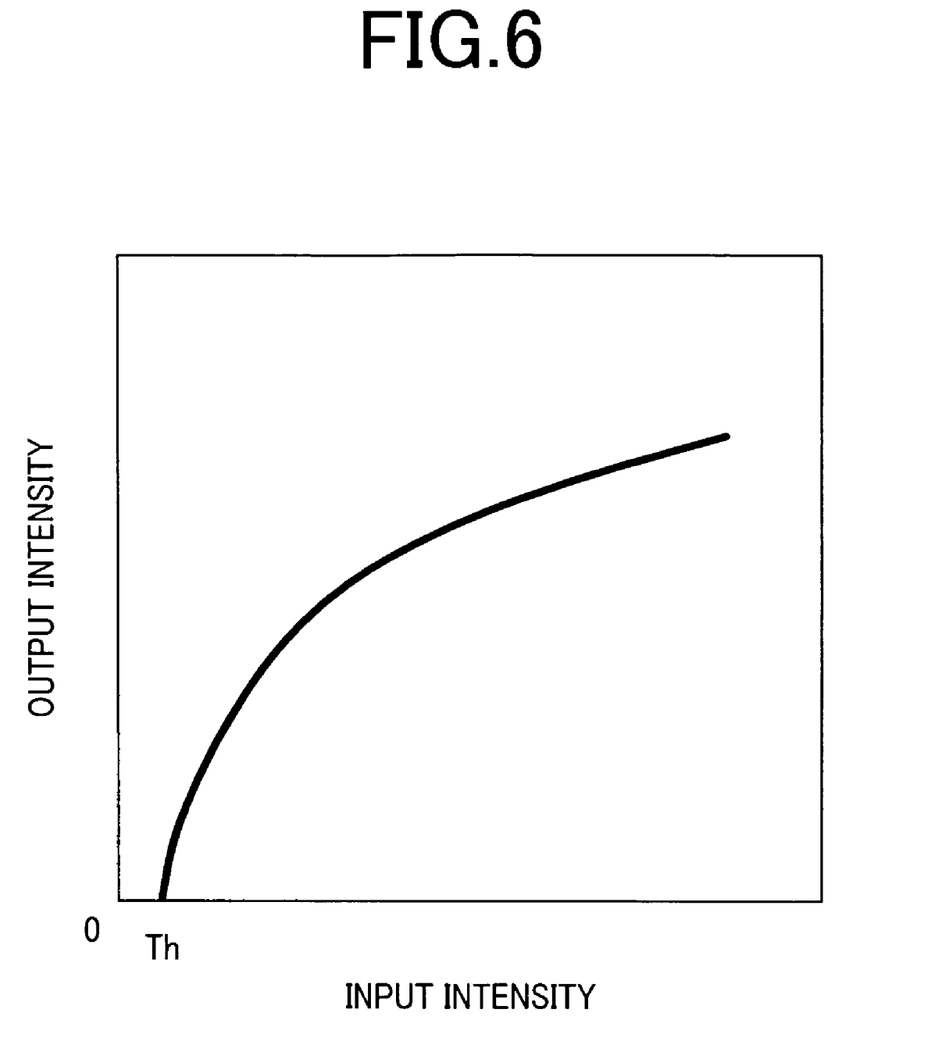
FIG. 6 is a diagram showing an intensity correction curve in the invention.
Figure 7A:
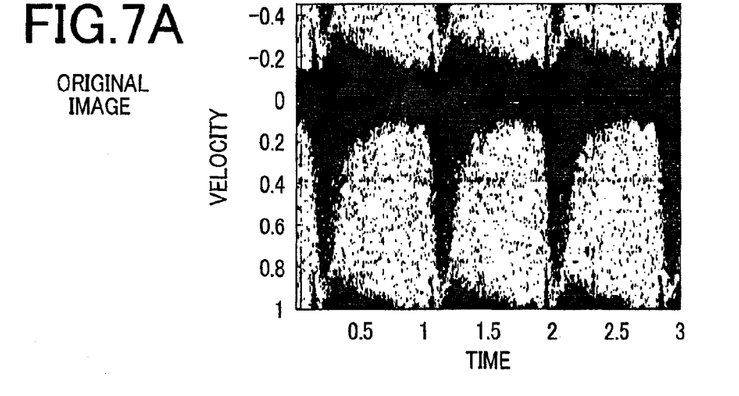
FIGS. 7A, 7B, and 7C are diagrams showing an original image, a blood flow spectrum image subjected to the intensity correcting process of the invention, and an image obtained by the conventional method, respectively.
Figure 7B:
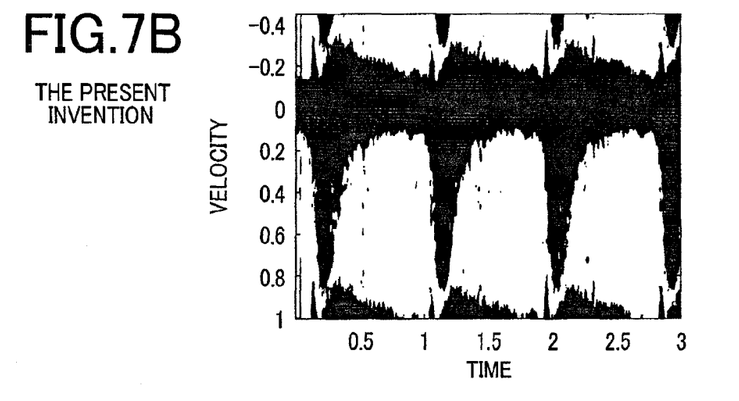
Figure 7C:
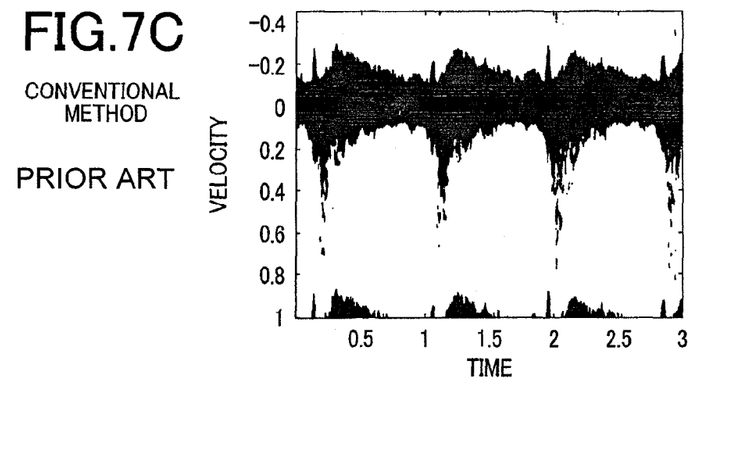

Intensity correction is performed by using the value Th and a γ curve shown in FIG. 6. FIGS. 7A to 7C are provided for comparison between the case of performing the intensity correcting process using a blood flow spectrum image (7b) subjected to the intensity correcting process according to the present invention and the case of performing the intensity correcting process using the known method (c) described in the conventional technique (Patent Document 1). FIGS. 7A to 7C show results of reverse videos so that comparison can be made easily.

The noise component is suppressed more in the method (b) according to the present invention and the known method (c) than the original image shown in FIG. 7A. When the signal areas are compared with each other, the signal intensity distribution of the method according to the present invention is continuous and it can be recognized that so-called black patch does not occur. The effect of the present invention can be recognized not only by comparison in visibility of images but also in the case where a contour is auto-traced.

Figure 8A:
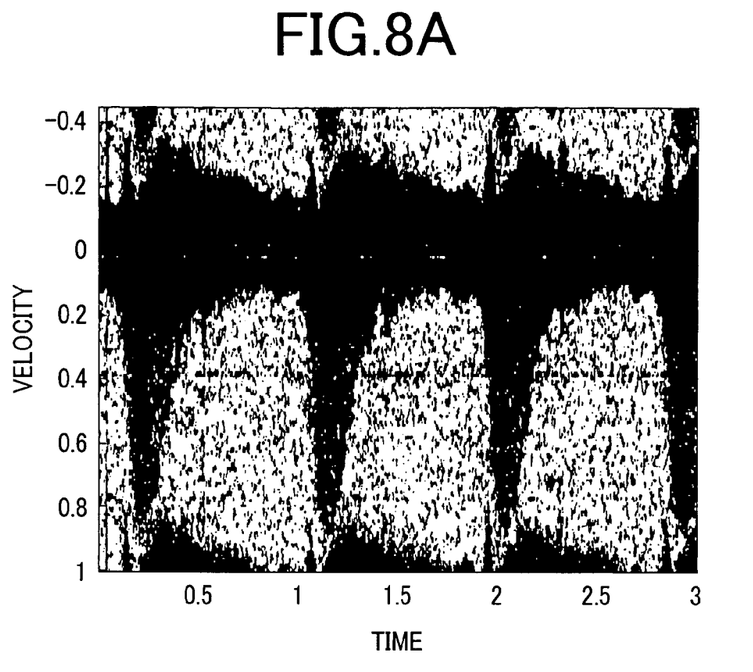
FIGS. 8A and 8B are diagrams showing a result of performing contour auto trace on the original image, and a result of performing contour auto trace on the blood flow spectrum image according to the present invention.
Figure 8B:
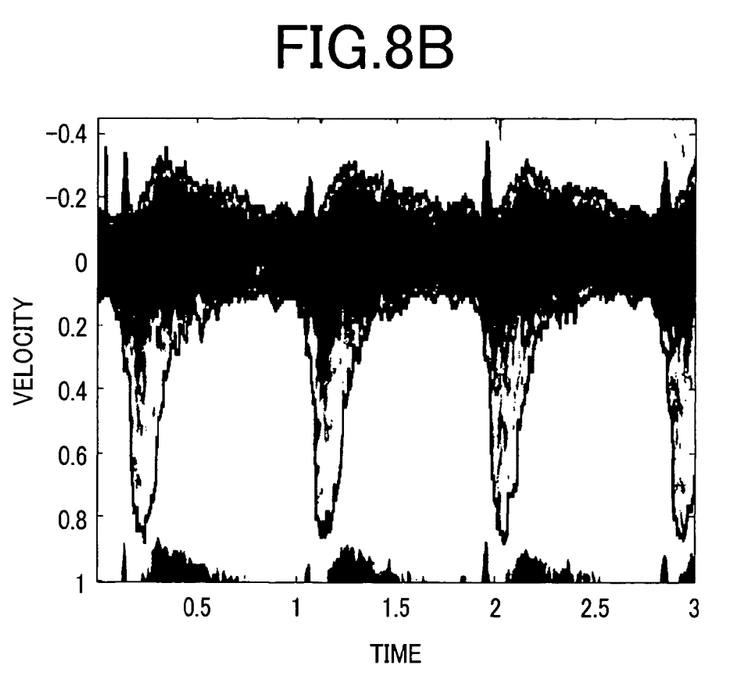

FIGS. 8A and 8B are also provided to show comparison between results of performing contour auto-trace on the original image and an image subjected to the image process of the present invention, respectively. FIGS. 8A and 8B show results of reverse videos so that comparison can be made easily.

In the result of performing the contour auto-trace on the original image (FIG. 8A), a deviation occurs between the contour of the signal component distribution and the result of auto trace. In the result of auto-trace after the process of the present invention (FIG. 8B), it is understood that the contour of the signal component distribution and the auto trace result match each other extremely.

Although histograms are always measured in the above description, depending on the performance of a computation circuit of the device, by providing a mechanism for detecting an environmental change, the histogram measurement can be omitted by using the value Th once obtained as long as the environmental change is not detected. The environmental change denotes a change in setting of the device or a change in a signal obtaining part. The environmental change can be detected by monitoring a representative value indicative of a parameter on the device side such as a statistical parameter such as the frequency of transmission/reception, and the number of sampling points of frequency conversion in the Doppler processing unit, or representative values indicative of statistical parameter of a signal such as an average value of Doppler signals, variance, pulse repetition frequency. By simplifying the histogram measurement, a real-time process can be performed in a small circuit-scale.

The parameter α (the half width of the Gaussian value) may be provided as a key in the interface 5 (FIG. 1). As the parameter α, a predetermined value may be used. A value with which the signal component peak can be detected on the histogram most excellently may be retrieved and used. Further, α for obtaining the value Th and α of the gray-level concentration filter use for outputting an image may be the same or different from each other.

INDUSTRIAL APPLICABILITY

As described in detail above, according to the present invention, the ultrasonographic device with improved visibility in a contour shape of signal components by suppressing display intensity of a noise component while minimizing the influence on display of the signal component in an ultrasonic blood flow spectrum image can be realized. By clarifying the contour of a spectrum waveform, detection of a lesion can be facilitated.

The invention claimed is:

1. An ultrasonic diagnostic apparatus comprising:
an ultrasonic probe;
a transmitter having a transmission signal generating circuit for generating a ultrasonic wave made by continuous wave or pulse wave and selectively transmitting the ultrasonic wave to a subject via the ultrasonic probe;
a receiver for phasing a reception signal received from the subject by the ultrasonic probe;
a Doppler processing unit for calculating Doppler frequency shift in the reception signal output from the receiver and calculating blood flow velocity of the subject on the basis of the Doppler frequency shift;
a display for displaying a time-varying waveform of the blood flow velocity;
a controller for controlling the transmitter, the receiver, the Doppler processing unit, and the display; and
a gray-level correcting unit for correcting gray level of an output result of the Doppler processing unit,
wherein the gray-level correcting unit includes a filtering unit for separating a signal and a noise from each other, which are included in the time-varying waveform of the blood flow velocity of the subject obtained by the Doppler processing unit, with a correcting gray level of pixels of the time-varying waveform by using weighting values determined by a weighting function on the basis of differences between the gray level of each of the pixels and a gray level of each of the peripheral pixels thereof on a space defined by the blood flow velocity and time, and a gray-level corrector for performing a gray level correction using, as a parameter, a boundary value between signal intensity and noise intensity obtained by the filtering unit.

2. The ultrasonic diagnostic apparatus according to claim 1, wherein the gray-level correction unit is constructed so as to suppress an intensity signal lower than the boundary value in intensity distribution of the signal and the noise.

3. The ultrasonic diagnostic apparatus according to claim 1, wherein the filtering unit includes means for defining a peripheral pixel range of the peripheral pixels in the time-varying waveform on the blood flow velocity, and means for determining the weighting value by the weighting function on the basis of the differences between the gray level of each of the pixels and the gray level of each of peripheral pixels in the peripheral pixel range.

4. The ultrasonic diagnostic apparatus according to claim 1, wherein the filtering unit obtains the boundary value with using the signal and the noise as peaks on a histogram from each other.

5. An ultrasonic diagnostic apparatus comprising:
an ultrasonic probe;
a transmitter having a transmission signal generating circuit for generating a ultrasonic wave made by continuous wave or pulse wave and selectively transmitting the ultrasonic wave to a subject via the ultrasonic probe;
a receiver for phasing a reception signal received from the subject by the ultrasonic probe;
a Doppler processing unit for calculating Doppler frequency shift in the reception signal output from the receiver and calculating blood flow velocity of the subject on the basis of the Doppler frequency shift;
a display for displaying a time-varying waveform of the blood flow velocity;
a controller for controlling the transmitter, the receiver, the Doppler processing unit, and the display; and
a gray-level correcting unit for correcting gray level of an output result of the Doppler processing unit,
wherein the gray-level correcting unit separates a signal and a noise from each other which are included the time-varying waveform of the blood flow velocity of the subject obtained by the Doppler processing unit, with a correcting gray level of pixels of the time-varying waveform by using weighting values determined by a weighting function on the basis of differences between the gray level of each of the pixels and a gray level of each of the peripheral pixels thereof on a space defined by the blood flow velocity and time, and performs an intensity correction by suppressing output intensity equal to or lower than a boundary point between signal intensity and noise intensity obtained as a result the separation of the signal and the noise.

6. The ultrasonic diagnostic apparatus according to claim 5, wherein the gray-level correcting unit obtains the boundary value based on the signal and the noise as peaks on a histogram from each other.

* * * * *